(12) United States Patent
Neumann

(10) Patent No.: US 12,101,300 B2
(45) Date of Patent: Sep. 24, 2024

(54) METHODS AND SYSTEMS OF TELEMEDICINE DIAGNOSTICS THROUGH REMOTE SENSING

(71) Applicant: KPN INNOVATIONS, LLC., Lakewood, CO (US)

(72) Inventor: Kenneth Neumann, Lakewood, CO (US)

(*) Notice: Subject to any disclaimer, the term of this patent is extended or adjusted under 35 U.S.C. 154(b) by 0 days.

(21) Appl. No.: 18/108,913

(22) Filed: Feb. 13, 2023

(65) Prior Publication Data

US 2023/0198955 A1    Jun. 22, 2023

Related U.S. Application Data

(63) Continuation of application No. 17/087,736, filed on Nov. 3, 2020, now Pat. No. 11,582,200, which is a (Continued)

(51) Int. Cl.
*G16H 40/67* (2018.01)
*A61B 5/00* (2006.01)
(Continued)

(52) U.S. Cl.
CPC ............ *H04L 63/04* (2013.01); *A61B 5/0022* (2013.01); *A61B 5/7221* (2013.01); (Continued)

(58) Field of Classification Search
None
See application file for complete search history.

(56) References Cited

U.S. PATENT DOCUMENTS 9,361,021 B2    6/2016    Jordan et al.
9,980,644 B2    5/2018    Fried et al.
(Continued)

OTHER PUBLICATIONS

Human Activity Recognition using Machine Learning Classification Techniques. Gulzar. IJITEE. (Year: 2019).*
(Continued)

*Primary Examiner* — Venkat Perungavoor
(74) *Attorney, Agent, or Firm* — Caldwell Intellectual Property Law

(57) ABSTRACT

A system for telemedicine diagnostics through remote sensing includes a computing device configured to initiate a communication interface between the computing device and a client device operated by a human subject, wherein the secure communication interface includes an audiovisual streaming protocol, receive, from at least a remote sensor at the human subject, a plurality of current physiological data, generate a clinical measurement approximation as a function of the change of a first discrete and a second discrete set of current physiological data, wherein generating further comprises receiving approximation training data correlating physiological data with clinical measurement data, training a measurement approximation model as a function of the training data and a machine-learning process, and generating the clinical measurement approximation as a function of the current physiological data and the measurement approximation model, and presenting the clinical measurement approximation to a user of the computing device using the secure communication interface.

20 Claims, 6 Drawing Sheets

Related U.S. Application Data continuation of application No. 16/939,373, filed on Jul. 27, 2020, now Pat. No. 10,931,643.

(51) Int. Cl.
| | | |
|---|---|---|
| *G16H 10/20* | (2018.01) | |
| *G16H 50/20* | (2018.01) | |
| *G16H 50/30* | (2018.01) | |
| *G16H 50/50* | (2018.01) | |
| *G16H 80/00* | (2018.01) | |
| *H04L 9/40* | (2022.01) | |
| *H04L 65/65* | (2022.01) | |
| *G06F 21/62* | (2013.01) | |
| *G06Q 50/00* | (2012.01) | |

(52) U.S. Cl.
CPC .......... *A61B 5/7267* (2013.01); *A61B 5/7465* (2013.01); *G16H 10/20* (2018.01); *G16H 40/67* (2018.01); *G16H 50/20* (2018.01); *G16H 50/30* (2018.01); *G16H 80/00* (2018.01); *H04L 65/65* (2022.05); *G06F 21/6245* (2013.01); *G06Q 50/01* (2013.01); *H04L 63/0428* (2013.01)

(56) References Cited

U.S. PATENT DOCUMENTS

| | | | |
|---|---|---|---|
| 10,216,906 B2 | 2/2019 | Desgranges et al. | |
| 10,325,070 B2 | 6/2019 | Beale et al. | |
| 10,586,020 B2 | 3/2020 | Madhavan et al. | |
| 10,937,160 B1* | 3/2021 | Ricci | G06Q 30/0631 |
| 2012/0029303 A1 | 2/2012 | Shaya | |
| 2016/0135706 A1 | 5/2016 | Sullivan et al. | |
| 2016/0210435 A1 | 7/2016 | Neumann et al. | |
| 2017/0011179 A1 | 1/2017 | Arshad et al. | |
| 2017/0024537 A1 | 1/2017 | Ferlito | |
| 2017/0196497 A1 | 7/2017 | Ray et al. | |
| 2017/0308666 A1 | 10/2017 | Thomson et al. | |
| 2018/0035886 A1 | 2/2018 | Courtemanche | |
| 2018/0070864 A1 | 3/2018 | Schuster | |
| 2018/0172667 A1 | 6/2018 | Noskov et al. | |
| 2018/0303381 A1 | 10/2018 | Todd et al. | |
| 2019/0027256 A1 | 1/2019 | Singh et al. | |
| 2019/0090769 A1 | 3/2019 | Boleyn et al. | |
| 2019/0139641 A1 | 5/2019 | Itu et al. | |
| 2019/0147136 A1 | 5/2019 | Lu et al. | |
| 2019/0209022 A1 | 7/2019 | Sobol et al. | |
| 2019/0365332 A1* | 12/2019 | Fedichev | A61B 5/11 |
| 2019/0371466 A1 | 12/2019 | Nicolella et al. | |
| 2020/0205745 A1 | 7/2020 | Khosousi et al. | |
| 2020/0260956 A1 | 8/2020 | Lee et al. | |
| 2020/0260962 A1 | 8/2020 | Mouchantaf et al. | |
| 2020/0375491 A1 | 12/2020 | Yang et al. | |
| 2021/0137391 A1* | 5/2021 | Mak | A61B 5/7225 |
| 2021/0225510 A1 | 7/2021 | Yang et al. | |
| 2021/0267488 A1 | 9/2021 | Taghvaeeyan et al. | |
| 2021/0280322 A1* | 9/2021 | Frank | G16H 50/20 |
| 2022/0044780 A1* | 2/2022 | Mason | G16H 80/00 |
| 2022/0115133 A1 | 4/2022 | Mason et al. | |

OTHER PUBLICATIONS

Detecting Diseases by Human-Physiological-Parameter-Based Deep Learning. Liu. IEEE. (Year: 2019).*
U.S. Appl. No. 16/919,674, filed Jul. 19, 2022, Kenneth Neumann.
https://www.researchgate.net/profile/Scott_Sittig/publication/335276477_Risk_Analysis_of_Residual_Protected_Health_Information_of_Android_Telehealth_Apps_Completed_Research_Full_Paper/links/5d5c30dd92851c37636e103a/Risk-Analysis-of-Residual-Protected-Health-Information-of-Android-Telehealth-Apps-Completed-Research-Full-Paper.pdf.
https://www.ncbi.nlm.nih.gov/pmc/articles/PMC5716614/pdf/ijt-09-3.pdf.
Green Cognitive Body Sensor Network: Architecture, Energy Harvesting, and Smart Clothing-Based Applications. Miao et al. IEEE.
Sensors, Vision and networks: From video surveillance to activity recognition and health monitoring. Prati et al. JAISE. (Year: 2019).
Artificial intelligence in emergency medicine. Liu et al. JECCM. (Year: 2018).
A Critical Review for Developing Accurate and Dynamic Predictive Models Using Machine Learning Methods in Medicine and Health Care. Alanazi et al. JMS. (Year: 2017).

* cited by examiner

METHODS AND SYSTEMS OF TELEMEDICINE DIAGNOSTICS THROUGH REMOTE SENSING

CROSS-REFERENCE TO RELATED APPLICATIONS

This application is a continuation of Nonprovisional application Ser. No. 17/087,736 filed on Nov. 3, 2020, and entitled "METHODS AND SYSTEMS OF TELEMEDICINE DIAGNOSTICS THROUGH REMOTE SENSING," which is a continuation of Nonprovisional application Ser. No. 16/939,373 filed on Jul. 27, 2020, and entitled "METHODS AND SYSTEMS OF TELEMEDICINE DIAGNOSTICS THROUGH REMOTE SENSING," the entirety of which is incorporated herein by reference.

FIELD OF THE INVENTION

The present invention generally relates to the field of network communication. In particular, the present invention is directed to methods and systems of telemedicine diagnostics through remote sensing.

BACKGROUND

Network connections can be susceptible to attack, leading to publication of private and sensitive information. Frequently, this can leave users unable to securely communicate, particularly in situations in need of immediate attention.

SUMMARY OF THE DISCLOSURE

In an aspect, a system for generating telemedicine diagnostics through remote sensing includes a computing device configured to receive, from a sensor, a plurality of current physiological data associated with the human subject, wherein the plurality of current physiological data includes a first discrete set of current physiological data and a second discrete set of current physiological data, calculate a change in physiological data between the first discrete set of current physiological data and the second discrete set of current physiological, generate a clinical measurement approximation as a function of the change between the first discrete set and the second discrete set, wherein generating includes receiving approximation training data correlating physiological data with clinical measurement data, training a measurement approximation model as a function of the training data and a machine-learning process, and generating the clinical measurement approximation as a function of the current physiological data and the measurement approximation model.

In another aspect, a method for generating telemedicine diagnostics and follow-up actions through remote sensing includes a computing device configured for receiving, from a sensor a plurality of current physiological data associated with the human subject, wherein the plurality of current physiological data includes a first discrete set of current physiological data and a second discrete set of current physiological data, calculating a change in physiological data between the first discrete set of current physiological data and the second discrete set of current physiological, generating a clinical measurement approximation as a function of the change between the first discrete set and the second discrete set, wherein generating includes receiving approximation training data correlating physiological data with clinical measurement data, training a measurement approximation model as a function of the training data and a machine-learning process, and generating the clinical measurement approximation as a function of the current physiological data and the measurement approximation model.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

Embodiments disclosed herein use classification of remote sensor data to clinical measurements to determine probable clinical measurement results during telemedicine sessions. Follow-up remote sensor capture may be performed based on confidence levels or user inputs. Detection of need for clinical measurements may be performed as well.

Figure 1:
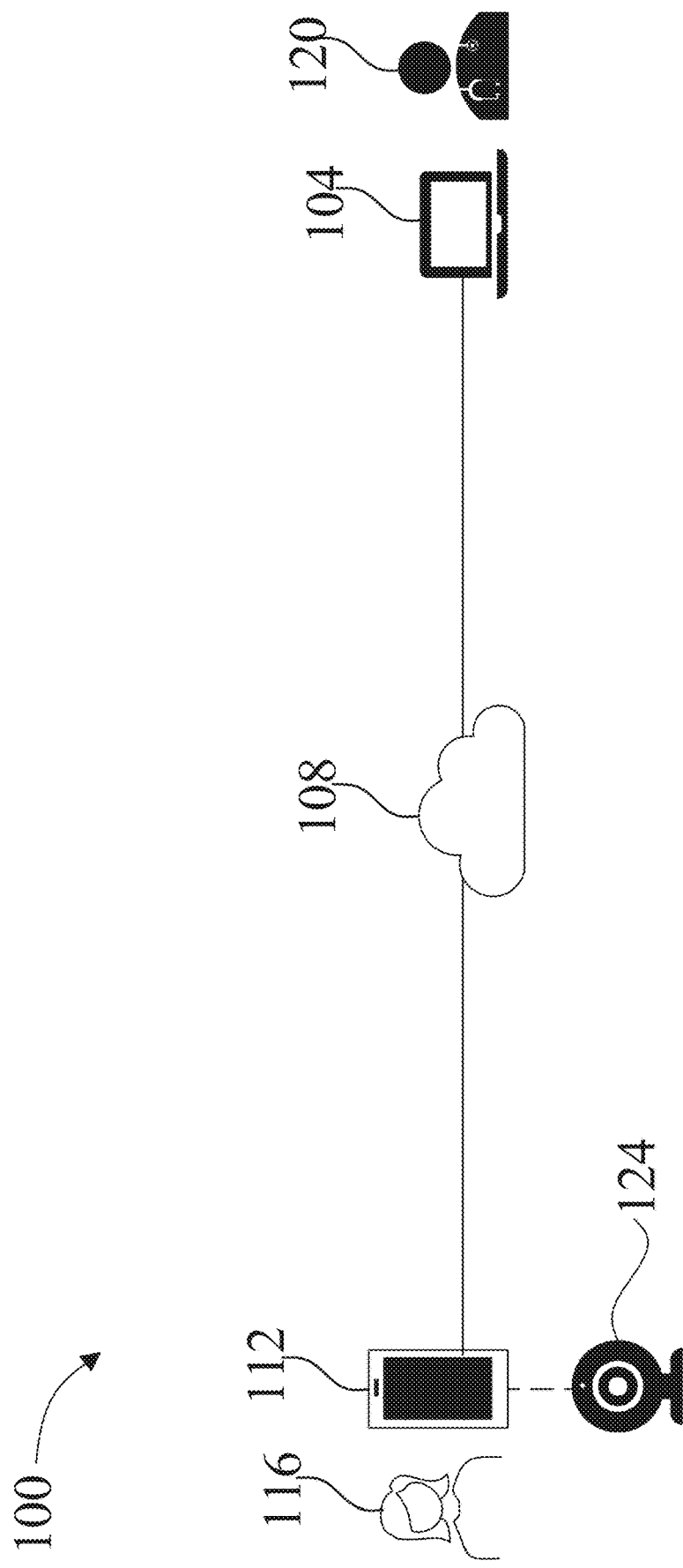
FIG. 1 is a schematic diagram of an exemplary embodiment of a system for telemedicine diagnostics through remote sensing.

Referring now to FIG. 1, an exemplary embodiment of a system for telemedicine diagnostics through remote sensing is illustrated. System includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently, or may include two or more computing device 104 operating in concert, in parallel, sequentially or the like; two or more computing devices may be included together in a single computing device 104 or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices in a first location and a second computing device 104 or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device 104, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device 104.

Computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 is configured to initiate a communication channel interface between the computing device 104 and a client device 112 operated by a human subject 116. A "human subject," as used in this disclosure, is a person at a client device 112 receiving telemedicine services such as a virtual doctor's visit, physical, "checkup," or the like. A "communication channel interface," as used in this disclosure, is a communication medium within an interface. A communication channel interface may include an application, script, and/or program capable of providing a means of communication between at least two parties, including any oral and/or written forms of communication. A communication channel interface may allow computing device 104 to interface with electronic devices through graphical icons, audio indicators including primary notation, text-based user interfaces, typed command labels, text navigation, and the like. A communication channel interface may include slides or other commands that may allow a user 120 to select one or more options. A communication channel interface may include free form textual entries, where a user 120 may type in a response and/or message. A communication channel interface includes a display interface. Display interface includes a form or other graphical element having display fields, where one or more elements of information may be displayed. Display interface may display data output fields including text, images, or the like containing one or more messages. A communication channel interface may include data input fields such as text entry windows, drop-down lists, buttons, checkboxes, radio buttons, sliders, links, or any other data input interface that may capture user interaction as may occur to persons skilled in the art upon reviewing the entirety of this disclosure. A communication channel interface may be provided, without limitation, using a web browser, a native application, a mobile application, and the like.

With continued reference to FIG. 1, computing device 104 initiates a communication channel interface with a client device 112. A "client device," as used in this disclosure, is a second computing device 104, including for example a mobile device such as a smartphone, tablet, laptop, desktop, and/or any other type of device suitable for use as computing device 104. Client device 112 is operated by a human subject 116; human subject 116 may include a person to whom telemedicine services are being rendered, including without limitation a patient. Computing device 104 may initiate communication channel interface using any network methodology as described herein. In an embodiment, a communication channel interface may be utilized to facilitate communications between a client device 112 operated by a human subject 116, and computing device 104 which may be operated by a user 120; user 120 may include a doctor, nurse, nurse practitioner, medical technician, medical assistant, pharmacist, pharmacy technician, and/or any other medical professional. For example, client device 112 may be operated by a patient who is in communication with a medical professional operating computing device 104, and communication channel interface may be utilized to have a telemedicine appointment. In yet another non-limiting example, client device 112 may be operated by a first member of a support group, and computing device 104 may be operated by a second member of the support group, whereby communication channel interface may be utilized to facilitate support group meetings and secure communications between members of the support group.

Further referring to FIG. 1, display interface may include a secure display interface, which may be implemented, maintained, and/or validated according to any process as described in U.S. Nonprovisional application Ser. No. 16/919,674, filed on Jul. 2, 2020, and entitled "METHODS AND SYSTEMS FOR GENERATING A SECURE COMMUNICATION CHANNEL INTERFACE FOR STREAMING OF SENSITIVE CONTENT," the entirety of which is incorporated herein by reference.

With continued reference to FIG. 1, an as a non-limiting example, initiating a secure communication channel interface 108 may include transmitting to user client device 112 a configuration packet uniquely identifying computing device 104. A "configuration packet," as used in this disclosure, is an encrypted message including a non-public device identifier." An encrypted message includes any language that contains text, characters, and/or symbols that have been converted into an alternative form, such as but not limited to ciphertext. An encrypted message may include using an algorithm and/or a series of algorithms to transform plaintext messages into ciphertext. Encrypted messages may only be viewed in a non-encrypted from by decrypting it using a correct decryption key. Encrypted messages may be decrypted using both symmetric and asymmetric cryptographic key pairs, such as for example a public and private key pair. An encrypted message may be generated in a manner that complies with the Health Insurance Portability and Accountability Act (HIPPA) of 1996. A message may be encrypted using a pseudo-random encryption key generated by an algorithm. In one embodiment, a process of converting plaintext into ciphertext is known as "encryption." Encryption process may involve the use of a datum, known as an "encryption key," to alter plaintext. Cryptographic system may also convert ciphertext back into plaintext, which is a process known as "decryption." Decryption process may involve the use of a datum, known as a "decryption key," to return the ciphertext to its original plaintext form. In embodiments of cryptographic systems that are "symmetric," decryption key is essentially the same as encryption key: possession of either key makes it possible to deduce the other key quickly without further secret knowledge. Encryption and decryption keys in symmetric cryptographic systems may be kept secret and shared only with persons or entities that the user of the cryptographic system wishes to be able to decrypt the ciphertext. One example of a symmetric cryptographic system is the Advanced Encryption Standard ("AES"), which arranges plaintext into matrices and then modifies the matrices through repeated permutations and arithmetic operations with an encryption key.

With continued reference to FIG. 1, a "non-public device identifier," as used in this disclosure, is a decryption key that cannot be readily deduced without additional secret knowledge, such as for example, a private key. A non-public device identifier may include a randomly generated number that cannot be easily guessed. A non-public device identifier may be generated using a stream cipher and/or a block cipher. An encrypted message may be transmitted with a non-public device identifier, to initiate secure communication between computing device 104 and user client device 112.

With continued reference to FIG. 1, computing device 104 receives from user device 104 a confirmation authentication a configuration packet. A confirmation may include any message, that allows user client device 112 to confirm the identify and/or authenticity of computing device 104. A confirmation may be transmitted from user client device 112 to computing device 104 using any network methodology as described herein. In an embodiment, a confirmation authentication may include receiving from user client device 112 a configuration packet uniquely identifying user client device 112. In such an instance, computing device 104 may receive the configuration packet uniquely identifying user client device 112 and authenticate the configuration packet, and the identify of user client device 112. Computing device 104 establishes a communication exchange as a function of receiving from user client device 112, a confirmation authenticating the configuration packet. A communication exchange includes any telecommunication handshake that includes an automated process of communications between two or more participants, such as computing device 104 and user client device 112. A telecommunication handshake includes the exchange of information establishing protocols of communication at the start of communication before full communication commences. A telecommunication handshake may include exchanging signals to establish a communication link as well as to agree as to which protocols to implement. A telecommunication handshake may include negotiating parameters to be utilized between user client device 112 and computing device 104, including information transfer rate, coding alphabet, parity, interrupt procedure, and/or any other protocol or hardware features. A telecommunication handshake may include but is not limited to a transmission control protocol (TCP), simple mail transfer protocol (SMTP), transport layer security (TLS), Wi-Fi protected access (WPA), and the like.

With continued reference to FIG. 1, a communication channel interface includes an audiovisual capture device 124. An "audiovisual capture device," as used in this disclosure, is a device used to record sound and/or images. An audiovisual capture device 124 may include but is not limited to, a camera, a video camera, a mobile device, a recording device, a DVD player, a sensor, a television tuner, a video capture card, a universal serial bus (USB) audio and/or visual capture device, and the like. In an embodiment, an audiovisual capture device 124 may be located within client device 112.

Still referring to FIG. 1, communication interface includes an audiovisual streaming protocol. An "audiovisual streaming protocol," as used in this disclosure, is a packet-based communication protocol that streams video and/or audio data from one device to another and vice-versa. An audiovisual streaming protocol may support a "video chat" process whereby a user 120 of computer device can see real-time or near real-time footage of human subject 116, while human subject 116 may be able to see real-time or near real-time footage of user of computing device 104. User 120 of computing device 104 may include, without limitation, a doctor, physician, nurse practitioner, nurse, therapist, psychologist, medical technician, and/or any other medical professional and/or assistant thereof. Audiovisual streaming protocol may enable user to perform many actions of a medical visit virtually, for instance by having human subject 116 perform measurements of height and/or weight of human subject 116, by having human subject 116 present different body parts for inspection using audiovisual capture device 124, or the like.

Figure 2:
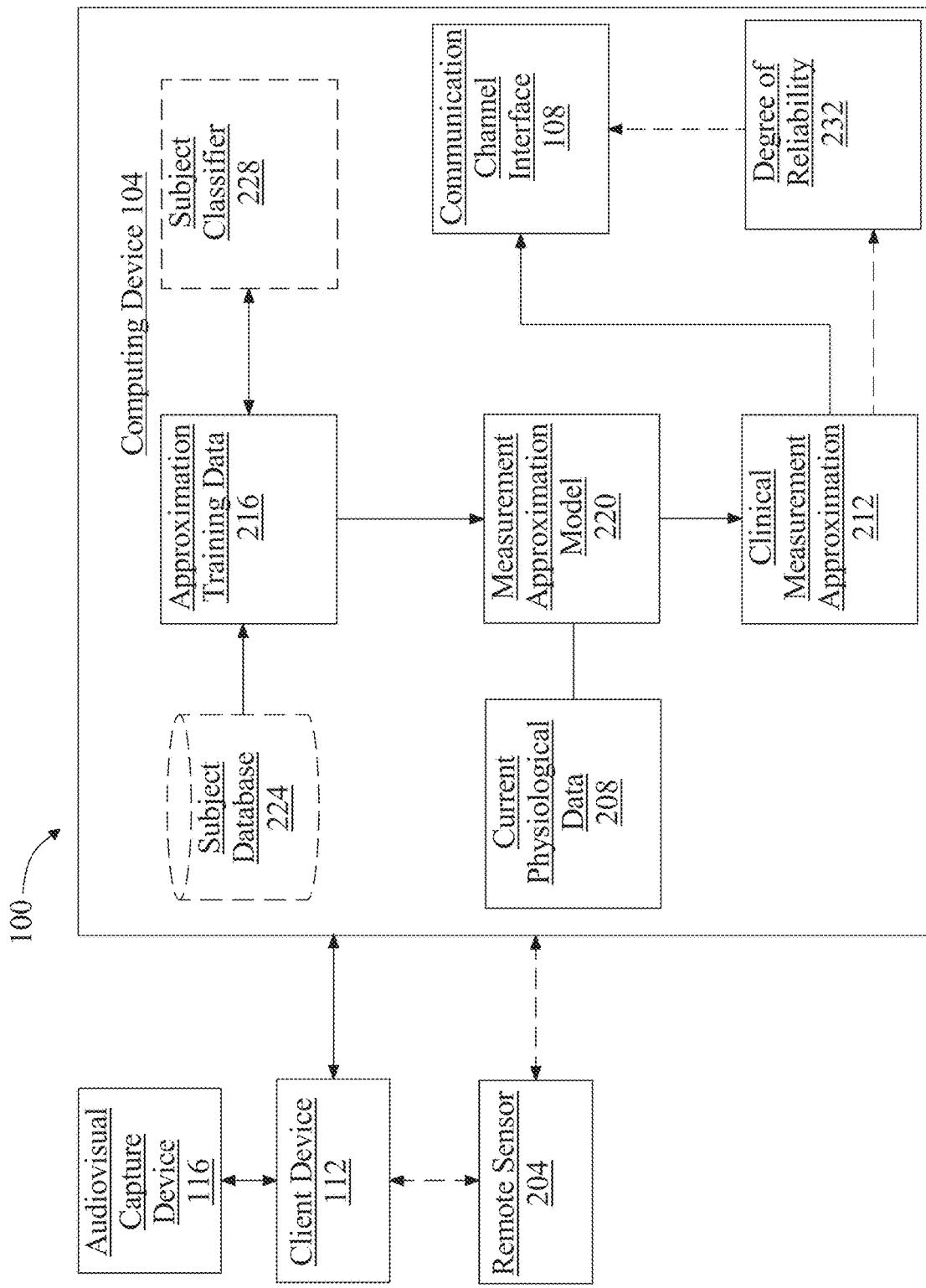
FIG. 2 is a block diagram of an exemplary embodiment of a system for telemedicine diagnostics through remote sensing.

Referring now to FIG. 2, computing device 104 is configured to receive a plurality of current physiological data 208 from at least a remote sensor 204 at the human subject 116. A "remote sensor," as used in this disclosure, is a device that captures data of human subject 116 and transmits that data to computing device 104, either by transmitting the data to client device 112 which relays the data to computing device 104, or by transmitting the data separately over a network connection. Data may be transmitted via communication channel interface and/or via a separate network connection formed, for instance, using a secure sockets layer (SSL) and/or hypertext transfer protocol-secure (HTTPS) process. Remote sensor 204 may include, without limitation, a camera such as a digital camera incorporated in a mobile device or the like, a microphone such as a mobile device microphone, a motion sensor, which may include one or more accelerometers, gyroscopes, magnetometer, or the like.

Remote sensor 204 may include one or more peripheral devices such as a peripheral pulse oximeter or the like. Remote sensor 204 may include a network-connected device such as a network connected digital scale or the like. In an embodiment, remote sensor 204 may be used to capture audio or visual data concerning one or more portions of human subject 116's anatomy. For instance, and without limitation, a microphone may be pressed against one or more portions of human subject 116 at direction of user 120 over communication channel, causing capture of audio data from the one or more portion of human subject 116; as a non-limiting example, audio data of human subject 116 lungs, heart, digestive system, or the like may be so captured. As a further example, user 120 may instruct human subject 116 to train a camera on one or more portions of anatomy to capture visual data concerning such one or more portions. Such physiological data may be combined; for instance, audio capture of circulatory system noise data may be combined with pulse oximetry data from a peripheral pulse oximeter and/or motion-sensor data indicating a degree of activity. Remote sensor 204 may include an electrical sensor such as a portable electrocardiogram device or the like. Generally, any sensor capable of capturing data of human subject 116 and transmitting such data locally or over a network may be used as a remote sensor 204.

Still referring to FIG. 2, plurality of current physiological data 208 may include cardiovascular data such as heart rate data, blood pressure data, or the like, for instance captured using audio and/or oximetry devices. Plurality of current physiological data 208 may include respiratory data such as audio capture of pulmonary sounds using a microphone or the like. Plurality of current physiological data 208 may include neurological data. Plurality of current physiological data 208 may include digestive audio data. Plurality of physiological data may include visual data captured regarding one or more elements of externally visible patient anatomy. Plurality of physiological data may capture one or more elements of human subject 116 bodily motion, including gait, posture, or gestural motions.

Still referring to FIG. 2, computing device 104 is configured to generate a clinical measurement approximation 212 as a function of the plurality of current physiological data 208. A "clinical measurement approximation," as used in this disclosure, is a numerical value estimating a likely clinical measurement matching plurality of current physiological data 208. A clinical measurement approximation 212 may function as approximation of what a doctor would get in person. For instance, a clinical measurement approximation 212 may approximate a heart rate, blood pressure, oxygen level, or other "vital sign" that might be captured in a clinical setting. In an embodiment, remote sensor 204 data may lack accuracy of clinically measured data and/or may not measure a given clinically measured datum directly. For instance, heart rate and/or blood oxygen as measured by home equipment, mobile devices, and/or mobile device peripherals may be less accurate than similar measurements captured using professional equipment. As a further non-limiting example, remote sensors 204 available at human subject 116 and/or client device 112 may not measure blood pressure directly but may measure a combination of cardiovascular parameters having some correlation, singly or in combination, with blood pressure, which may be used in some combination to estimate blood pressure levels. Persons skilled in the art, upon reviewing the entirety of this disclosure, will be aware of various clinical measurement approximations 212 that may be generated. A user 120 of computing device 104 may use one or more clinical measurement approximations 212, in combination with other information obtained by communicating with human subject 116 and/or clinical history of human subject 116, to arrive at conclusions concerning a state of health of human subject 116.

Figure 3:
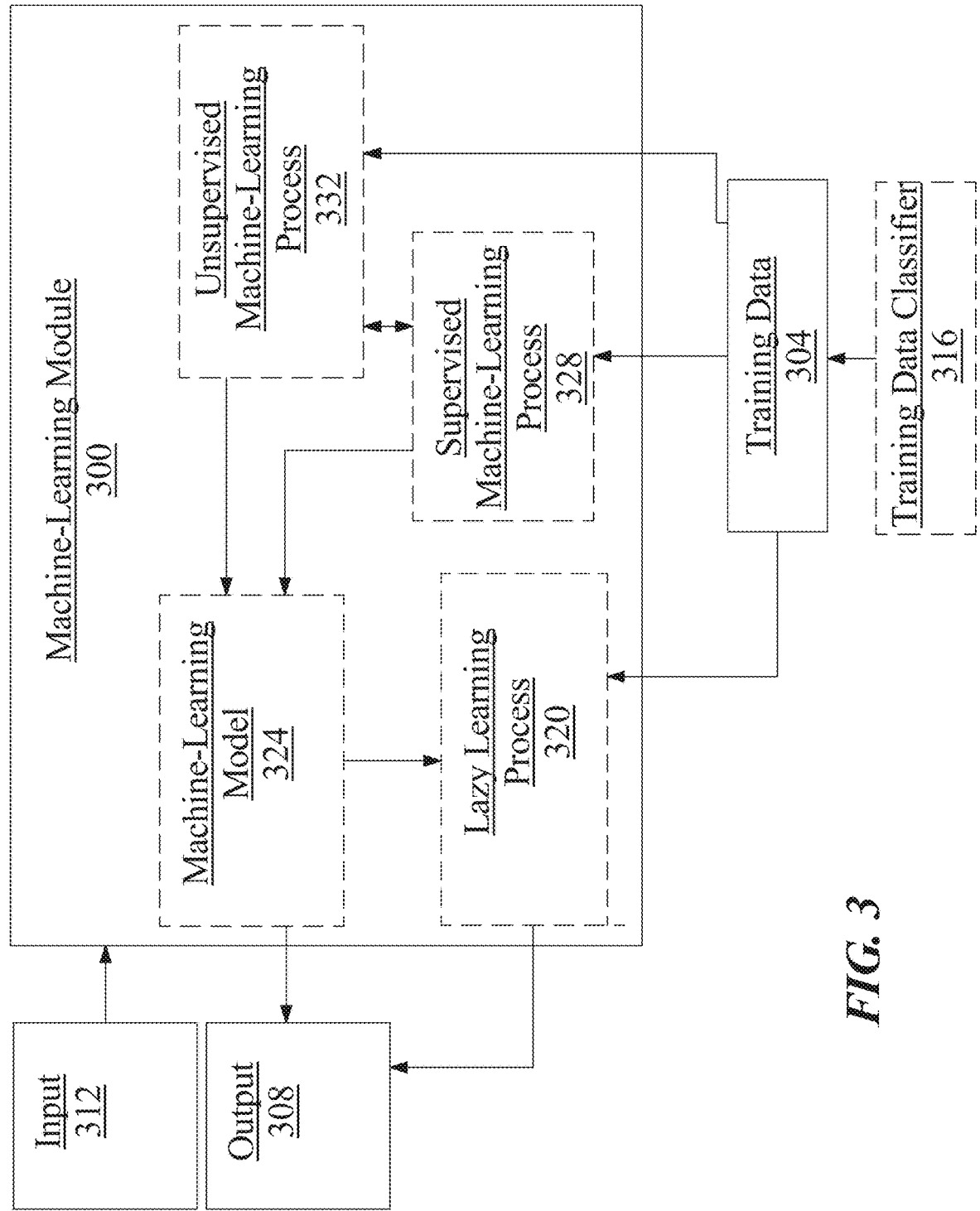
FIG. 3 is a block diagram of an exemplary embodiment of a machine-learning module.

Referring to FIG. 3, generation of clinical measurement approximation 212 may be performed using a machine-learning process. Referring now to FIG. 3, an exemplary embodiment of a machine-learning module 300 that may perform one or more machine-learning processes as described in this disclosure is illustrated. Machine-learning module may include any suitable Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm that will be performed by a computing device 104/module to produce outputs 308 given data provided as inputs 312; this is in contrast to a non-machine learning software program where the commands to be executed are determined in advance by a user 120 and written in a programming language.

Still referring to FIG. 3, "training data," as used herein, is data containing correlations that a machine-learning process may use to model relationships between two or more categories of data elements. For instance, and without limitation, training data 304 may include a plurality of data entries, each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 300 may generate a classifier using a classification algorithm, defined as a process whereby a computing device 104 and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to a cohort of persons and/or clinical data having similarities to data of human subject 116 and/or current physiological data 208

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively, or additionally, and with continued reference to FIG. 3, machine-learning processes as described in this disclosure may be used to generate machine-learning models 324. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs as described in this disclosure as inputs, outputs as described in this disclosure as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 3, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data 304.

Referring again to FIG. 2, and as a non-limiting example, computing device 104 may be configured to generate clinical measurement approximation 212 by receiving approximation training data 216 correlating physiological data with clinical measurement data, training a measurement approximation model 220 as a function of the training data and a machine-learning process, and generating the clinical measurement approximation 212 as a function of the current physiological data 208 and the measurement approximation model 220. "Clinical measurement data," as used in this disclosure is data describing measurements taken in a clinical setting such as a doctor's office with clinical equipment, such as a blood pressure cuff, stethoscope, or the like. Approximation training data 216 may be collected, without limitation, by taking simultaneous clinical measurements and remote sensor 204 measurements of human subject 116 and/or other persons over one or more in-person clinical visits, for instance and without limitation according to examples as described in further detail below.

Further referring to FIG. 2, generating clinical measurement approximation 212 may include identifying at least a category of current physiological data 208 and classifying the at least a category of current physical data to the measurement approximation model 220 and/or to approximation training data 216 used to train approximation model. Classification may be performed using a classifier, as described above, which may match physiological data sets to one or more input sets suitable for one or more clinical measurement approximation 212. For instance, and without limitation, current physiological data 208 may contain a first set of data that may be used to approximate a first clinical measurement, and a second set of data that may be used to approximate a second clinical measurement; in this case, classification may identify both such clinical measurements and machine-learning models and/or training data that may be used to approximate each. Where the same clinical measurement may be approximated by a first set of physiological measurement data or a second set of physiological measurement data, classifier may identify both, and computing device 104 may determine which set of physiological measurement data produces a more reliable result, for instance as calculated below; a measurement approximation model 220 associated with the more reliable set may be selected for use by computing device 104.

Still referring to FIG. 2, training measurement approximation model 220 may include generating a general model. General model may be a first measurement approximation model 220 trained with general approximation training data 216, as described above, concerning multiple persons, where each entry may be obtained as described above. A population of persons that general approximation training data 216 describes may be a randomly selected population of patients and/or a population of patients chosen according to one or more characteristics shared with human subject 116, where one or more characteristics may include demographic data such as age, sex, ethnicity, region of residence, or the like, diagnostic data such as shared illnesses, conditions, and/or preconditions, other data such as user habits, or the like. Such data may be tracked and stored for each patient in a subject database 224.

Figure 4:
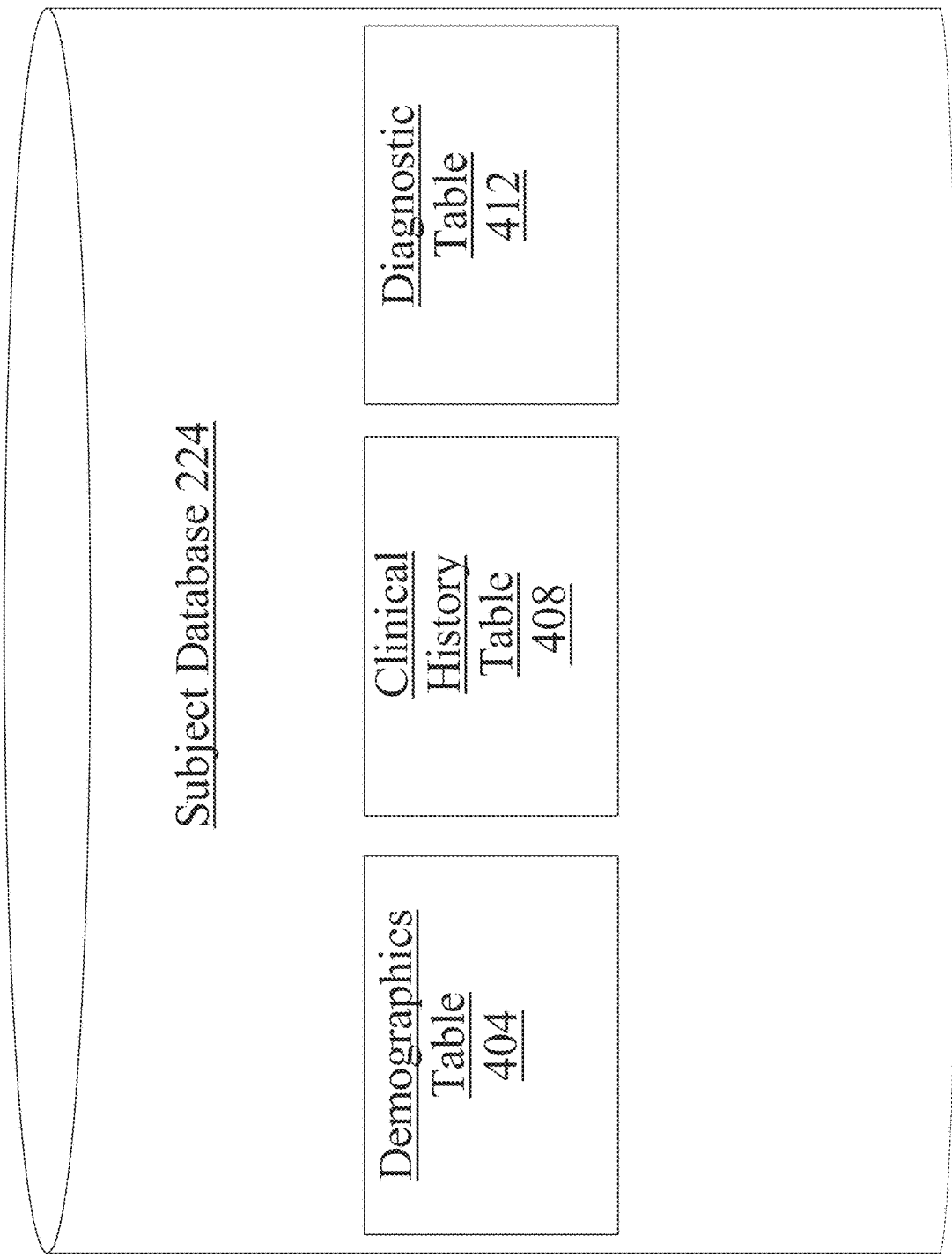
FIG. 4 is a block diagram of an exemplary embodiment of a subject database.

Referring now to FIG. 4, an exemplary embodiment of a subject database 224 is illustrated. Subject database may be implemented, without limitation, as a relational subject database, a key-value retrieval subject database such as a NOSQL subject database, or any other format or structure for use as a subject database that a person skilled in the art would recognize as suitable upon review of the entirety of this disclosure. Subject database may alternatively or additionally be implemented using a distributed data storage protocol and/or data structure, such as a distributed hash table or the like. Subject database may include a plurality of data entries and/or records as described above. Data entries in a subject database may be flagged with or linked to one or more additional elements of information, which may be reflected in data entry cells and/or in linked tables such as tables related by one or more indices in a relational subject database. Persons skilled in the art, upon reviewing the entirety of this disclosure, will be aware of various ways in which data entries in a subject database may store, retrieve, organize, and/or reflect data and/or records as used herein, as well as categories and/or populations of data consistently with this disclosure. Subject database 224 may include one or more tables, including without limitation a demographics table 404; demographics table may include demographic information concerning human subject 116, including without limitation age, ethnicity, location of residence, national origin, sex, or the like. Subject database 224 may include a clinical history table 408, which may contain previously captured clinical measurements of human subject 116 and/or related sensor measurements. Subject database 224 may include a diagnostic table 412, which may contain one or more diagnoses, prognoses, and/or other prognostic data concerning human subject 116.

Referring again to FIG. 2, approximation training data 216 and/or general approximation training data 216 may alternatively or additionally be matched to human subject 116 using a subject classifier 228. Subject classifier 228, which may include any classifier as described above, may classify approximation training data 216 to one or more patient categories, and may then classify human subject 116 to one or more such patient categories; corresponding training data may be used to train a general approximation model, which training may be performed after classification of human subject 116 and/or concurrently or prior to such classification. In an embodiment, a general approximation model may enable computing device 104 to approximate a given clinical measurement for persons in given cohort and/or for persons generally, providing a "first guess" regarding human subject 116, which may be used for further steps of process and/or used as an initial step in a human subject 116—specific training process.

Still referring to FIG. 2, computing device 104 may further train general approximation model using subject-specific training data, defined herein as approximation training data 216 collected using clinical measurements and corresponding remote sensor 204 data regarding human subject 116 specifically. This data may be collected in one or more live clinical visits. In an embodiment, training a subject-specific model from a general approximation model may enable a relatively sparse set of subject-specific training data to be used to generate an accurate subject-specific model.

In an embodiment, and with further reference to FIG. 2, training measurement approximation model 220 may include classification of the human subject 116 to approximation training data 216; for instance in lieu of use of use of subject-specific training data, training data classified to human subject as above may be used to generate approximation model.

In an embodiment, and still referring to FIG. 2, generating clinical measurement approximation 212 may include calculating a change between a first discrete data set of plurality of current physiological data 208 and a second discrete set of current physiological data 208 and generating clinical measurement approximation 212 as a function of the change. A "discrete set" of data, as used in this disclosure, is a set of data that may be definitely separated from another discrete set, such as data separated by an interval in time, taken with a different category of remote sensor 204, or the like. A difference between first discrete set and second discrete set may be used in some embodiments as an input to approximation model. In other words, some embodiments of system may use a change in sensor feedback from a first discrete measurement to a second discrete measurement captured after the first discrete measurement, and/or captured through a distinct channel, to generate clinical measurement approximation 212. First discrete set of current physiological data 208 may be temporally separated from second discrete set of current physiological data 208, where "temporal separation" indicates that a period of time, which may be a time in seconds, minutes, hours, days, or the like, separates the two sets. Period of time may be determined by a user 120 of computing device 104, such as a doctor or other medical professional.

Still referring to FIG. 2, computing device 104 may be configured to record the first discrete set of current physiological data 208, generate a prompt instructing the human subject 116 to perform an activity, and record the second discrete set of current physiological data 208. For instance, and without limitation, where the clinical measurement to be approximated is a cardiovascular measurement, activity may include some degree of physical exertion such as squats, running in place, walking around the room, bending down to touch toes, or the like. As a further example, activity may include consuming a food, liquid, or other substance, positioning a sensor by moving from a first position used to capture first data set to a second position used to capture second data set (e.g., motion from front of torso to rear of torso of a microphone), or the like. Computing device 104 may be configured to verify that the human subject 116 has performed the activity. Verification may be performed, without limitation, by way of visual confirmation by a user 120 of computing device 104, such as without limitation a doctor or other medical professional.

Still referring to FIG. 2, computing device 104 is configured to present clinical measurement approximation 212 to a user 120 of computing device 104 using the communication interface. User 120 of computing device 104 may include, without limitation, a doctor or other medical professional. Computing device 104 may be configured to determine a degree of reliability 232 of the clinical measurement and provide the degree of reliability 232 using the communication interface. A "degree of reliability," as used in this disclosure, is a probability that clinical measurement approximation 212 matches a corresponding clinical measurement. Degree of reliability 232 may be computed, without limitation, using a terminal error function result in generation of approximation model; for instance, where error function was iteratively minimized during training, minimal error function resulting from training process may be converted to an error and/or error probability percentage. Computing device 104 may be configured to identify a follow-up action as a function of the degree of reliability 232. For instance, and without limitation, computing device 104 may compare degree of reliability 232 to a preconfigured threshold number, such as a probability of accuracy above a threshold percentage; falling below the threshold number may cause computing device 104 to determine that more information is needed. Alternatively or additionally, a user 120 of computing device 104 such as a doctor or other medical professional may view degree of reliability 232 as displayed to the user 120, may conclude that further information is needed for a more accurate result, and may enter an instruction via computing device 104 and/or interface indicating that a follow-up action is needed.

Further referring to FIG. 2, follow-up action may include one or more additional readings using remote sensors 204, which may include duplicate readings, readings taking using a different sensor and/or set of sensors, readings temporally separated from a first set of readings, for which changes as described above may be used as an input, or the like. A new set of remote sensor 204 readings may be combined with an original set as inputs to approximation model and/or may be input to approximation model separately; in either case, reliability of second output may be evaluated for improvement in reliability, and process may be repeated until reliability exceeds a threshold number as described above and/or a user 120 of computing device 104 enters a command indicating satisfaction. Follow-up action may alternatively or additionally include a clinical test corresponding to clinical measurement approximation 212. For instance, computing device 104 may output a suggestion to perform clinical test and/or a user 120 of computing device 104 may instruct human subject 116 to perform the clinical test and/or may order that a clinical test be performed. In an embodiment, processes described in this disclosure may enable a medical professional to determine when processes such as diagnostics using shipped samples, conveyance of more exact testing equipment to a location of human subject 116, and/or an in-person clinical visit are necessary or recommended.

Figure 5:
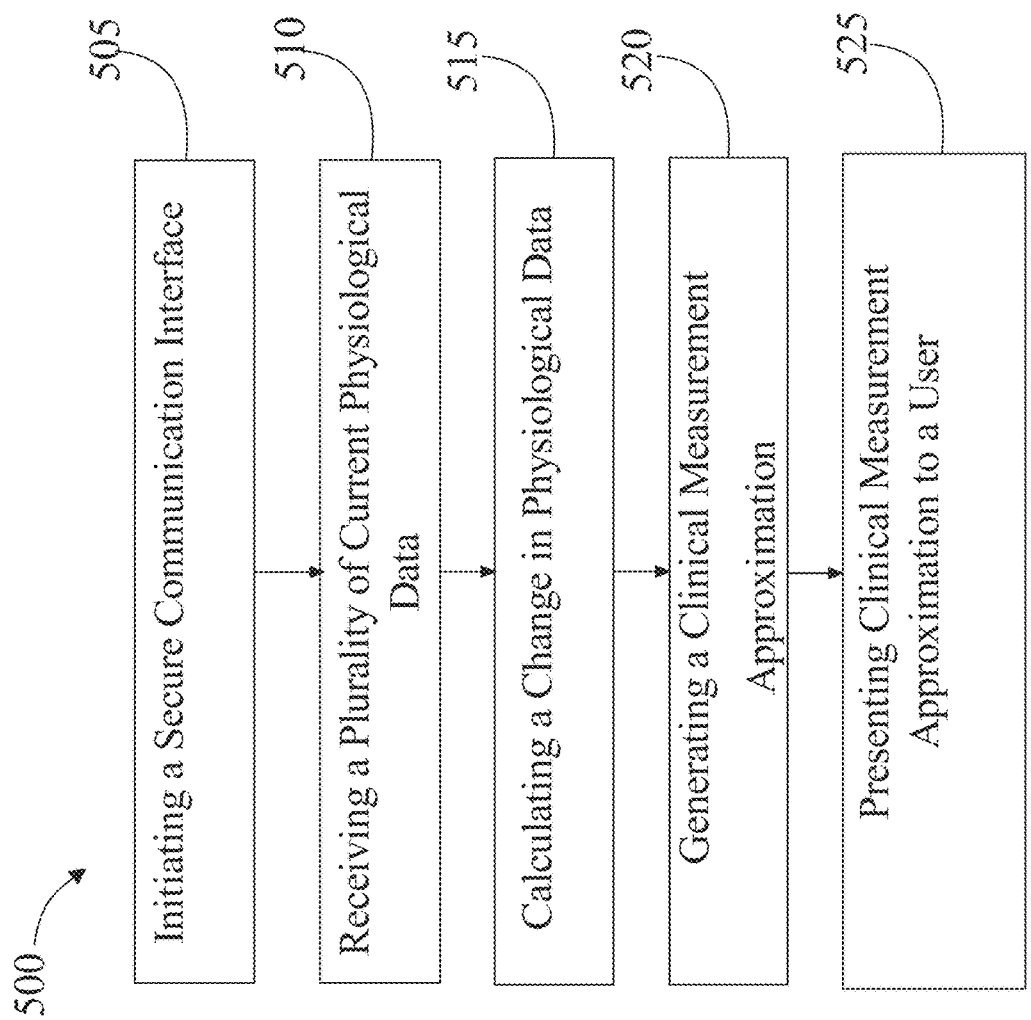
FIG. 5 is a flow diagram of an exemplary embodiment of a method of telemedicine diagnostics through remote sensing.

Referring now to FIG. 5, an exemplary embodiment of a method 500 of telemedicine diagnostics through remote sensing is illustrated. At step 505, a computing device 104 initiates a secure communication interface between the computing device and a client device 112 associated with a human subject 116 and at a second location, wherein the secure communication interface includes an audiovisual streaming protocol; this may be implemented, without limitation, as described above in reference to FIGS. 1-4.

At step 510, and with continued reference to FIG. 5, computing device 104 receives, from at least a remote sensor 204 at the second location, a plurality of current physiological data 208 associated with the human subject 116, wherein the plurality of current physiological data 208 comprises a first discrete set of current physiological data and a second discrete set of current physiological data; this may be implemented, without limitation, as described above in reference to FIGS. 1-4.

At step 515, and still referring to FIG. 5, computing device 104 calculates a change in physiological data between the first discrete set of current physiological data 208 and the second discrete set of current physiological data 208; this may be implemented, without limitation, as described above in reference to FIGS. 1-4.

Continuing in reference to FIG. 5, at step 520, computing device 104 generates a clinical measurement approximation 212 as a function of the change between the first discrete set and the second discrete set, wherein generating includes receiving approximation training data correlating physiological data with clinical measurement data, training a measurement approximation model as a function of the training data and a machine-learning process, and generating the clinical measurement approximation as a function of the change in physiological data and the trained measurement approximation model. Training the clinical measurement approximation model may include classification of the human subject to the approximation training data. Training the measurement approximation model may include generating a general model as a function of general training data and training a subject-specific model as a function of subject-specific training data. The first discrete set of current physiological data is temporally separated from the second discrete set of current physiological data; this may be implemented, without limitation, as described above in reference to FIGS. 1-4.

Continuing in reference to FIG. 5, continuing at step 520, computing device 104 may be further configured to record the first discrete set of current physiological data, generate a prompt instructing the human subject to perform an activity, and record the second discrete set of current physiological data. The computing device 104 may be further configured to verify that the human subject has performed the activity. The computing device 104 may be configured to determine a degree of reliability of the first clinical measurement and provide the degree of reliability using the communication interface. Computing device 104 may be further configured to identify a follow-up action as a function of the degree of reliability. System 100 may include receiving an instruction via the computing device 104.

Further referring to FIG. 5, generating clinical measurement approximation 212 may include calculating a change between a first discrete data set of the plurality of current physiological data 208 and a second discrete set of current physiological data 208 and generating the clinical measurement approximation 212 as a function of the change in physiological data and the trained measurement approximation model. First discrete set of current physiological data 208 may be temporally separated from second discrete set of current physiological data 208. In an embodiment, computing device 104 may record first discrete set of current physiological data 208, generate a prompt instructing human subject 116 to perform an activity, and record second discrete set of current physiological data 208. Computing device 104 may verify that human subject 116 has performed the activity.

At step 525, and still referring to FIG. 5, computing device 104 is configured to present, via the audiovisual streaming protocol of the secure communication interface, the clinical measurement approximation to a user of the computing device 104; this may be implemented, without limitation, as described above in reference to FIGS. 1-4.

It is to be noted that any one or more of the aspects and embodiments described herein may be conveniently implemented using one or more machines (e.g., one or more computing devices that are utilized as a user computing device 104 for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device 104) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device 104) and any related information (e.g., data structures and data) that causes the machine to perform any one of the methodologies and/or embodiments described herein.

Examples of a computing device 104 include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device 104 may include and/or be included in a kiosk.

Figure 6:
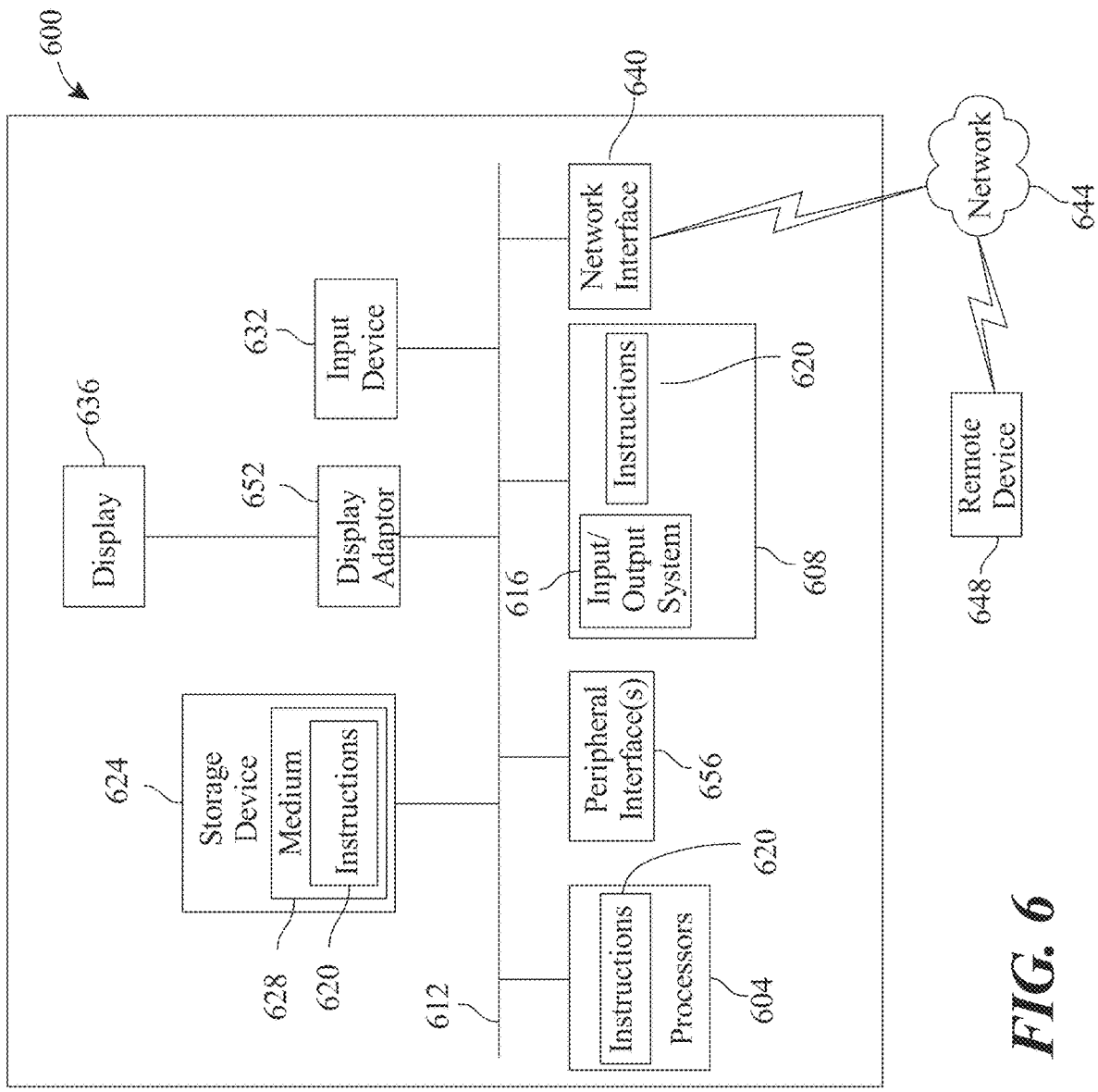
FIG. 6 is a block diagram of a computing system that can be used to implement any one or more of the methodologies disclosed herein and any one or more portions thereof.

FIG. 6 shows a diagrammatic representation of one embodiment of a computing device 104 in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Processor 604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIRE-WIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for telemedicine diagnostics through remote sensing, the system comprising:
    a computing device;
    a memory communicatively connected to the computing device, the memory containing instructions configuring the computing device to:
    receive, from a sensor, a plurality of current physiological data associated with a human subject, wherein the plurality of current physiological data comprises a first discrete set of current physiological data and a second discrete set of current physiological data; and
    calculate a change in physiological data between the first discrete set of current physiological data and the second discrete set of current physiological data; and
    generate a clinical measurement approximation, using a measurement approximation model, as a function of the change between the first discrete set and the second discrete set of the current physiological data, wherein generating the clinical measurement approximation further comprises:
        receiving an approximation training data set, wherein the approximation training data set comprises outputs correlated to inputs, wherein the inputs comprise physiological data and the outputs comprise clinical measurement data;
        training, iteratively, the measurement approximation model using the approximation training data set, wherein training the measurement approximation model includes retraining the measurement approximation model with feedback from previous iterations of the measurement approximation model; and
        generating the clinical measurement approximation as a function of the change in the physiological data and the trained measurement approximation model.

2. The system of claim 1, wherein generating the clinical measurement approximation further comprises:
    identifying a category of the first discrete set and the second discrete set of current physiological data; and
    classifying the category of the first discrete set and the second discrete set of the current physiological data to the measurement approximation model.

3. The system of claim 1, wherein generating the clinical measurement approximation comprises:
    generating a first clinical measurement approximation as a function of the first discrete set and a second clinical measurement approximation as a function of the second discrete set; and determining, by the measurement approximation model, a degree of reliability of the first clinical measurement approximation and the second measurement approximation as a function of the classification.

4. The system of claim 1, wherein the computing device is configured to determine a degree of reliability of the first clinical measurement by comparing the degree of reliability to a preconfigured threshold number.

5. The system of claim 4, wherein the computing device is configured to identify a follow-up action as a function of the degree of reliability.

6. The system of claim 1, wherein the memory contains instructions further configuring the computing device to:
  initiate a secure communication interface between the computing device and a client device associated with the human subject and at a second location, wherein the secure communication interface includes an audiovisual streaming protocol; and
  present using the audiovisual streaming protocol of the secure communication interface, the clinical measurement approximation to a user of the computing device.

7. The system of claim 6, wherein initiating the secure communication interface comprises transmitting to the client device a configuration packet uniquely identifying the computing device.

8. The system of claim 6, wherein initiating the secure communication interface further comprises receiving a confirmation authentication of the configuration packet.

9. The system of claim 6, wherein the audiovisual streaming protocol comprises a video chat process.

10. The system of claim 1, wherein the sensor comprises a camera.

11. The system of claim 1, wherein training the measurement approximation model further comprises:
  generating a general model as a function of general training data; and
  training a subject-specific model as a function of subject-specific training data.

12. The system of claim 1, wherein the first discrete set of current physiological data is temporally separated from the second discrete set of current physiological data.

13. The system of claim 1, wherein the computing device is further configured to:
  record the first discrete set of current physiological data;
  generate a prompt instructing the human subject to perform an activity; and
  record the second discrete set of current physiological data.

14. The system of claim 13, wherein the computing device is further configured to verify that the human subject has performed the activity.

15. A method for telemedicine diagnostics through remote sensing, the method comprising:
  receiving, by the computing device, from a sensor, a plurality of current physiological data associated with a human subject, wherein the plurality of current physiological data comprises a first discrete set of current physiological data and a second discrete set of current physiological data; and
  calculating, by the computing device, a change in physiological data between the first discrete set of current physiological data and the second discrete set of current physiological data;
  generating, by the computing device, a clinical measurement approximation, using a measurement approximation model, as a function of the change between the first discrete set and the second discrete set, wherein generating further comprises:
    receiving an approximation training data set, wherein the approximation training data set comprises outputs correlated to inputs, wherein the inputs comprise physiological data and the outputs comprise clinical measurement data;
    training, iteratively, the measurement approximation model using the approximation training data set, wherein training the measurement approximation model includes retraining the measurement approximation model with feedback from previous iterations of the measurement approximation model; and
    generating the clinical measurement approximation as a function of the change in physiological data and the trained measurement approximation model;
  presenting, by the computing device, using the clinical measurement approximation to a user of the computing device.

16. The method of claim 15, wherein generating the clinical measurement approximation comprises:
  generating a first clinical measurement approximation as a function of the first discrete set and a second clinical measurement approximation as a function of the second discrete set; and
  determining, by the measurement approximation model, a degree of reliability of the first clinical measurement approximation and the second measurement approximation as a function of the classification.

17. The method of claim 15, wherein the computing device is configured to determine a degree of reliability of the first clinical measurement by comparing the degree of reliability to a preconfigured threshold number.

18. The method of claim 15, wherein the computing device is configured to identify a follow-up action as a function of the degree of reliability.

19. The method of claim 13, wherein the audiovisual streaming protocol comprises a video chat process.

20. The method of claim 15, wherein the sensor comprises a camera.

* * * * *